United States Patent
Warlick et al.

(10) Patent No.: US 7,594,930 B2
(45) Date of Patent: *Sep. 29, 2009

(54) METHOD OF ATTACHING SOFT TISSUE TO BONE

(75) Inventors: John Warlick, Woodstock, GA (US);
Reiner Schultheiss, Illighausen (CH);
Wolfgang Schaden, Vienna (AT)

(73) Assignee: General Patent LLC, Marietta, GA (US)

( * ) Notice: Subject to any disclaimer, the term of this patent is extended or adjusted under 35 U.S.C. 154(b) by 393 days.

This patent is subject to a terminal disclaimer.

(21) Appl. No.: 11/458,413

(22) Filed: Jul. 19, 2006

(65) Prior Publication Data

US 2008/0009730 A1 Jan. 10, 2008

Related U.S. Application Data

(60) Provisional application No. 60/818,993, filed on Jul. 6, 2006.

(51) Int. Cl.
*A61F 2/08* (2006.01)
*A61H 1/00* (2006.01)
*A61H 1/02* (2006.01)
*A61H 5/00* (2006.01)

(52) U.S. Cl. .......................... 623/13.14; 601/2
(58) Field of Classification Search ............... 623/13.14, 623/13.11, 23.49; 600/439; 601/2
See application file for complete search history.

(56) References Cited

U.S. PATENT DOCUMENTS 4,244,370 A 1/1981 Furlow et al.

(Continued)

FOREIGN PATENT DOCUMENTS

EP   1 254 638   5/2000

(Continued)

OTHER PUBLICATIONS

R. Meirer, et al: Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier Ltd.

(Continued)

*Primary Examiner*—David Isabella
*Assistant Examiner*—Yashita Sharma
(74) *Attorney, Agent, or Firm*—David L King

(57) ABSTRACT

A method of attaching or reattaching a ligament, tendon, cartilage or other soft tissue to a bone mass has the steps of: positioning or placing the ligament, tendon, cartilage or other soft tissue adjacent to the bone mass; anchoring or otherwise fastening the ligament, tendon, cartilage or soft tissue to the bone mass; and transmitting shock waves to the ligament, tendon or other soft tissue and the bone mass. Preferably the ligament, tendon, cartilage or other soft tissue is positioned in the path of the emitted shock waves and away from geometric focal volume or point of the emitted shock waves. The shock waves may be transmitted during the surgical procedure or post operatively in one or more treatment dosages or both. In so treating the ligament, tendon, cartilage or other soft tissue should be positioned at a distance away from any geometric focal point to minimize hemorrhaging. The soft tissue may include cartilage or muscle tissue. In the case of cartilage, the tissue can be inserted into a bone mass prepared cavity and optionally anchored there by a covering bone plug.

4 Claims, 12 Drawing Sheets

U.S. PATENT DOCUMENTS

| | | | |
|---|---|---|---|
| 4,632,100 | A | 12/1986 | Somers et al. |
| 5,919,196 | A | 7/1999 | Bobic et al. |
| 6,068,596 | A | 5/2000 | Weth et al. |
| 6,113,560 | A | 9/2000 | Simnacher |
| 6,176,839 | B1* | 1/2001 | Deluis et al. .................... 601/2 |
| 6,413,230 | B1 | 7/2002 | Haupt et al. |
| 6,428,531 | B1 | 8/2002 | Visuri et al. |
| 6,537,319 | B2 | 3/2003 | Whelan |
| 6,554,824 | B2 | 4/2003 | Davenport et al. |
| 6,755,821 | B1 | 6/2004 | Fry |
| 6,875,216 | B2 | 4/2005 | Wolf |
| 6,916,333 | B2 | 7/2005 | Schmieding et al. |
| 7,063,717 | B2 | 6/2006 | St. Pierre et al. |
| 2003/0129154 | A1 | 7/2003 | McDaniel |
| 2003/0130599 | A1* | 7/2003 | Restle et al. .................... 601/2 |
| 2004/0167445 | A1 | 8/2004 | Simnacher |
| 2005/0021013 | A1 | 1/2005 | Visuri et al. |
| 2006/0004365 | A1 | 1/2006 | Schmieding et al. |
| 2006/0036195 | A1 | 2/2006 | Schultheiss et al. |
| 2006/0100550 | A1 | 5/2006 | Schultheiss et al. |
| 2008/0021353 | A1* | 1/2008 | Menzi et al. .................... 601/1 |

FOREIGN PATENT DOCUMENTS

| | | |
|---|---|---|
| JP | 2002-085418 | 3/2002 |
| JP | 2004-215862 | 8/2004 |
| WO | PCT/US 05/36455 | 10/2005 |

OTHER PUBLICATIONS

L. Gerdesmeyer, et al; Antibacterial Effects of Extracorporal Shock Waves; World Fed for Ultrasound in Medicine & Biology; printed USA; Elsevier, vol. 31, No. 1, pp. 115-119, 2005.

G. Haupt, et al; Effect of Shock Waves on the Healing of Partial-Thickness Wounds in Piglets; Journal of Surgical Research, vol. 49, No. 1, pp. 45-48, Jul. 1990 Copyright 1990 by Academic Press, Inc.

Jagadeesh, G. et al; "Novel applications of micro-shock waves in biological sciences", J. Indian Inst. Sci. 2002, 82, pp. 1-10.

Thiel, M. et al; "The use of shock waves in medicine-a tool of the modern OR; an overview of basic physical principles, history and research", Min Inves Ther & Allied Technol 2000; 9(3/4) 247-253.

Huemer, Georg M. et al; "Comparison of the effectiveness of gene therapy with transforming growth factor-B or extracorporal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005;13:262-268).

* cited by examiner

METHOD OF ATTACHING SOFT TISSUE TO BONE

RELATED APPLICATIONS

This application claims benefit of priority to U.S. Provisional Patent Application Ser. No. 60/818,993 filed Jul. 6, 2006 entitled Method of Attaching Soft Tissue to Bone, the disclosure of which is incorporated herein by reference in its entirety.

FIELD OF THE INVENTION

The invention relates to an improved method of attaching soft tissue to bone, more particularly one of the methods relates to the use of shock waves combined with mechanical fasteners to accelerate healing and increase attachment adhesion, another deals with enhancing cartilage transplant healing.

BACKGROUND OF THE INVENTION

In severe injuries ligaments, tendons and muscle tissue surrounding the bones can be torn or otherwise detached from the skeletal structure. Often the ligaments or tendons are so damaged that they must be replaced using cadaver ligaments or tendons or other sources of such tissue. In other cases tissue such as cartilage is worn or degenerated and the repair includes transplanting typically from the patient/donor.

Whether detached tissue is repairable or if replacement tissue is required, the primary goal of the surgeon is to insure the tissue is held securely against the bone mass or internal thereto so the detached tissue or implanted tissue can grow and physically attach itself or reattach to the bone.

Sutures are commonly used in such procedure. A number of methods for securing a tissue to a body part have been disclosed. U.S. Pat. No. 4,244,370 taught the use of positioning an implant within the soft body tissue, but was not concerned with anchoring the tissue to the bone mass. Improvements of attachment involve the anchoring of the tissue directly to the bone mass. U.S. Pat. No. 4,632,100 and U.S. Pat. No. 6,916,333 both teach novel anchors for use in such procedures. U.S. Pat. No. 6,875,216 disclosed the use of a tapered bioabsorbable interference screw for endosteal fixation of ligaments and U.S. Pat. No. 7,063,717 teaches a bio-interference screw fixation technique that is particularly beneficial in anterior cruciate ligament (ACL) reconstruction.

Regardless of the procedure or technique employed each of these prior art systems rely on the body's ability to facilitate a permanent reattachment to the bone. Accordingly these mechanical fasteners improve the successful outcome of the surgery only to the extent the patient's body responds properly as is true in any surgical procedure.

Accordingly the period of time immediately after surgery and during rehabilitation are critical in that the reconstructed ligaments or tendons are more susceptible to damage until regrowth and reattachment to the bone mass occurs. Similarly in the case of cartilage transplants the removal of healthy cartilage and placement in a damaged area from a donor/patient is a common practice which is taught in U.S. Pat. No. 5,919,196. The resultant holes in the removal site and the transplant site need to have the surrounding bone and tissue grow in to the cavities for proper healing.

With young healthy patients the time to achieve regrowth is usually quicker, but the natural high activity of these patients' means that the risk of re-injury is greater during the time after surgery and prior to full attachment.

Conversely more elderly patients require a longer time to achieve reattachment, but are less active generally and therefore the risk of re-injury is over a longer time, but at a lower presumed level.

In either group of patients, the need exists to reduce the time required to achieve reattachment of the ligament or tendons to the bone mass or acceptance of the cartilage transplant to insure a successful recovery and full use of the limb.

In PCT patent application PCT/US 05/36455 a novel method of using non focused shock waves was disclosed to treat a variety of conditions within tissues and organs. The US patent priority applications were 2006/0100550 A1 and 2006/0036195 A1 which are incorporated herein by reference. This use of such shock waves in combination with mechanical fastening of tendons or ligaments is described below.

SUMMARY OF THE INVENTION

A method of attaching or reattaching a ligament, tendon, cartilage or other soft tissue to a bone mass has the steps of: positioning or placing the ligament, tendon, cartilage or other soft tissue adjacent or internal to the bone mass; anchoring or otherwise holding or fastening the ligament, tendon, cartilage or soft tissue to the bone mass; and transmitting shock waves to the ligament, tendon, cartilage or other soft tissue and the bone mass. Preferably the ligament, tendon, cartilage or other soft tissue is positioned in the path of the emitted shock waves and away from geometric focal volume or point of the emitted shock waves. The shock waves may be transmitted during the surgical procedure or post operatively in one or more treatment dosages or both. In so treating the ligament, tendon, cartilage or other soft tissue should be positioned at a distance away from any geometric focal point to minimize hemorrhaging. The soft tissue may include cartilage or muscle tissue. In the case of cartilage, the tissue can be inserted into a bone mass prepared cavity and optionally anchored there by a covering bone plug.

The transmitted shock waves are emitted using an applicator device which may be used by placing it inside a disposable sterile sleeve or cover. In such a case the applicator can be simply cleaned with a disinfecting agent prior to use as it is not directly exposed to the tissue. Alternatively the applicator without a sleeve or cover can be used wherein the applicator should be sterilized prior to use. In either use the sleeve or cover or the applicator without a cover should be coupled acoustically to the treated tissue or organ by a sterile coupling fluid or viscous gel like ultrasound gels or even NaCl solution to avoid transmission loss. Additionally a sterile cover or foil may be placed surrounding the treatment site.

DEFINITIONS

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"extracorporeal" occurring or generated outside the living body.

A "generalized paraboloid" according to the present invention is also a three-dimensional bowl. In two dimensions (in Cartesian coordinates, x and y) the formula $y^n=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z, +z)), with z being a measure for the burn down of an electrode, and n, so that phenomena including, but not limited to, burn down of the tip of an electrode (−z, +z) and/or disturbances caused by diffraction at the aperture of the paraboloid are compensated for.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (µs) for the positive part of a cycle and typically above some microseconds for the negative part of a cycle Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

When soft tissue tears away from bone, reattachment becomes necessary. Various devices including sutures alone, screws, staples, wedges and plugs have been used to secure soft tissue to the bone. Recently various types of threaded suture anchors have been employed for this purpose. Suture anchors are fasteners that are screwed into predrilled holes or otherwise self-tapping into a bone mass such that the suture anchor can be embedded in the bone mass wherein a suture can be placed through an opening in the anchor which can therefore be used to tie the ligaments, tendons or other soft tissue to the bone structure. This means to anchor the soft tissue around the bone insures that the ligament or tendon stays in a position that is most suitable for repair in that during the healing process the ligament or tendon can reattach itself to the underlying bone structure without being displaced or otherwise remain unattached.

Figure 13:
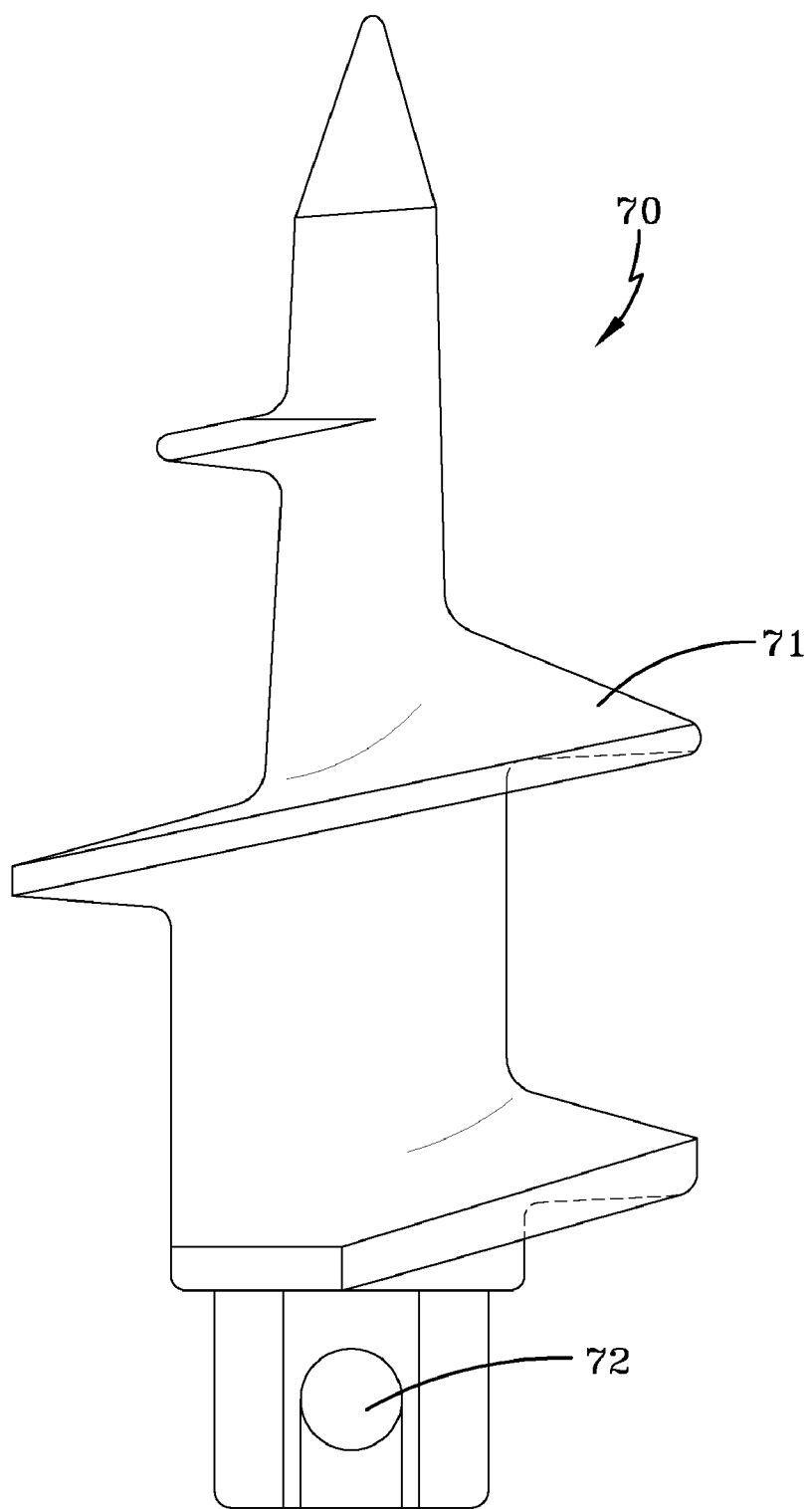
FIG. 13 is a plan view of a fastener/anchor through which a suture can be inserted to secure a ligament or tendon.

As shown in FIG. 13, a representative suture anchor 70 is shown of a corkscrew type threaded fastener that improves the pull out characteristics of the anchor 70 when installed in soft bone tissue or bone mass 101. Other fasteners with less dramatic pitch on the screw threads 71 are known to be used to also provide this function of anchoring ligaments, tendons or other soft onto the bone structure. The corkscrew anchor 70 as illustrated in FIG. 13 is fully described in U.S. Pat. No. 6,916,333 B2 and is incorporated by reference herein in its entirety. The opening 72 provides a way to attach the ligament or tendon to the bone mass 101 when installed a suture is tied to the opening and then around the tissue to secure it against the bone mass 101.

Figure 14:
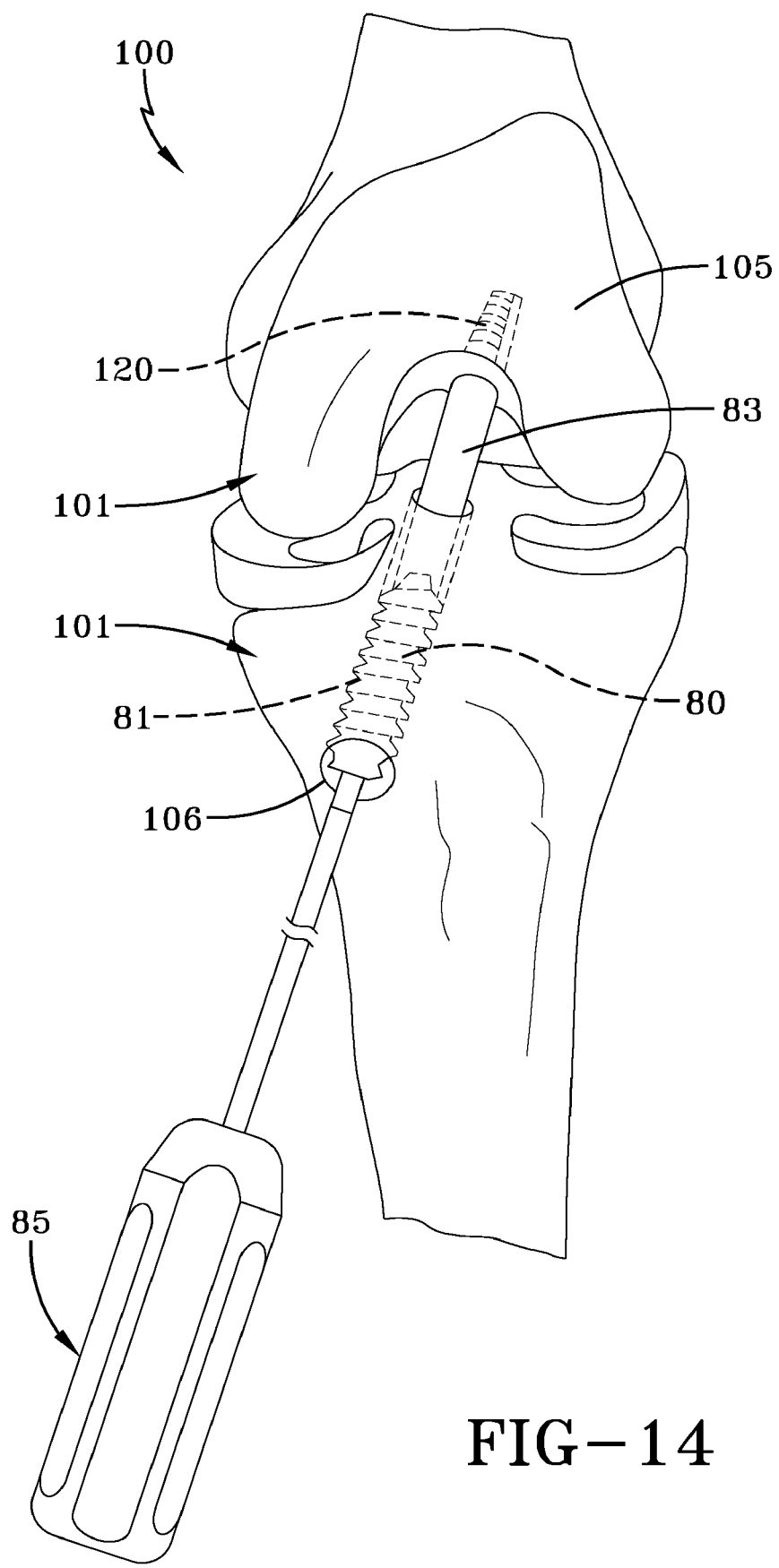
FIG. 14 is a perspective view of a portion of a bone mass having a ligament attached.

With reference to FIG. 14 a tapered bioabsorbable interference screw for endosteal fixation of ligaments 120 is illustrated. It is described in detail in U.S. Pat. No. 6,875,216 B2. The bioabsorbable interference screw 80 preferably has the threads 81 along the entire length of the screw shaft and is used in ACL reconstruction wherein the graft preferably a hamstring tendon graph is secured, preferably by interference screw fixation installation on device 85 in a femoral socket 105 formed through the tibial tunnel 106 as described for example in U.S. Pat. No. 5,320,626; the disclosure of which is incorporated herein by reference in its entirety. The hamstring graft has been drawn taught and secured in the tibial tunnel 106 by insertion of the bioabsorbable interference screw 80 which can be fully cannulated, a guide pin 83 may optionally be employed to guide the interference screw during the delivery and installation. These and other aspects of the methodology of securing such a ligament are taught in detail in U.S. Pat. No. 6,875,216 B2 which is incorporated herein by reference in its entirety.

Figure 15:
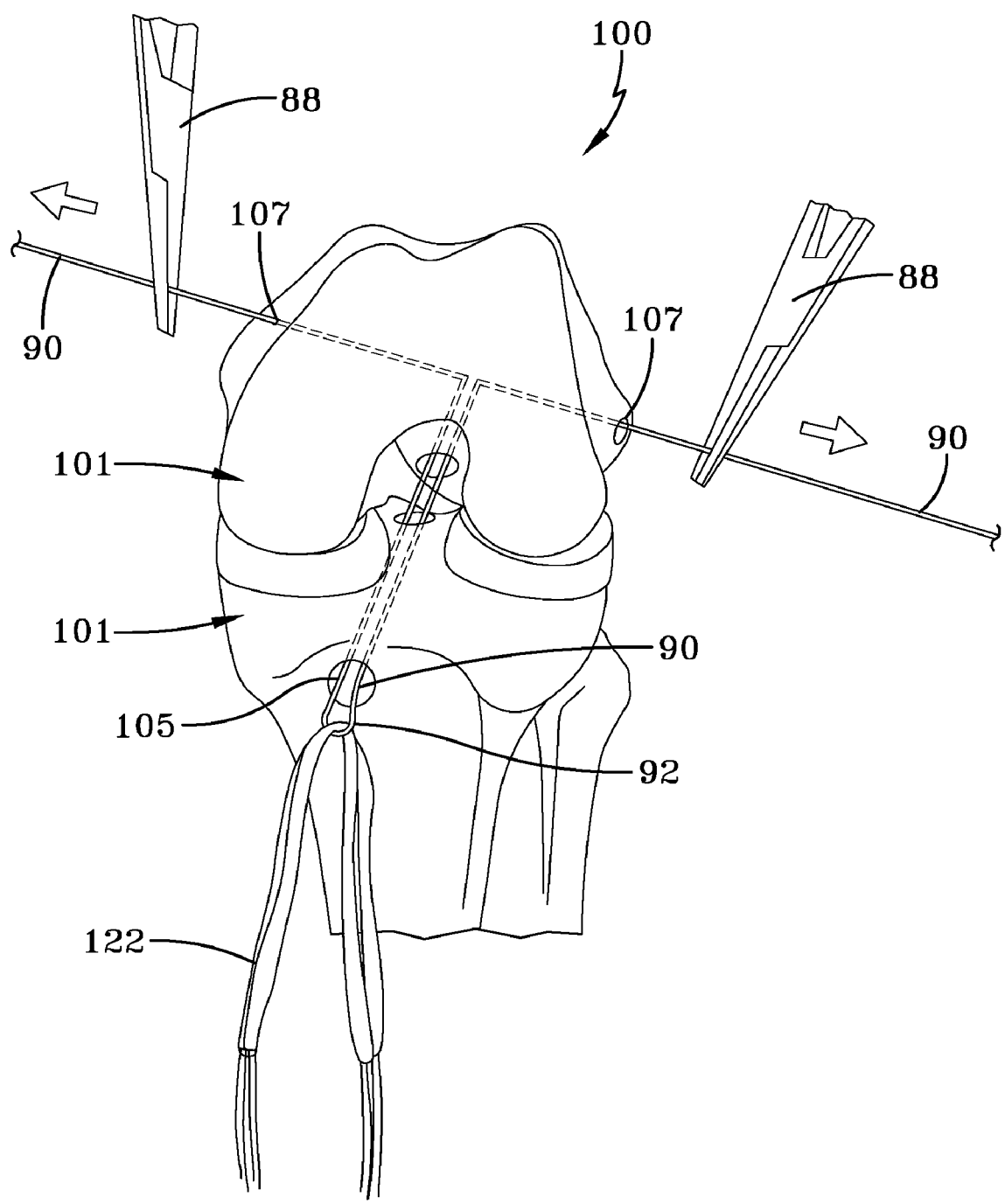
FIG. 15 is a perspective view of a portion of a bone mass having a tendon inserted into a knee joint.
Figure 16:
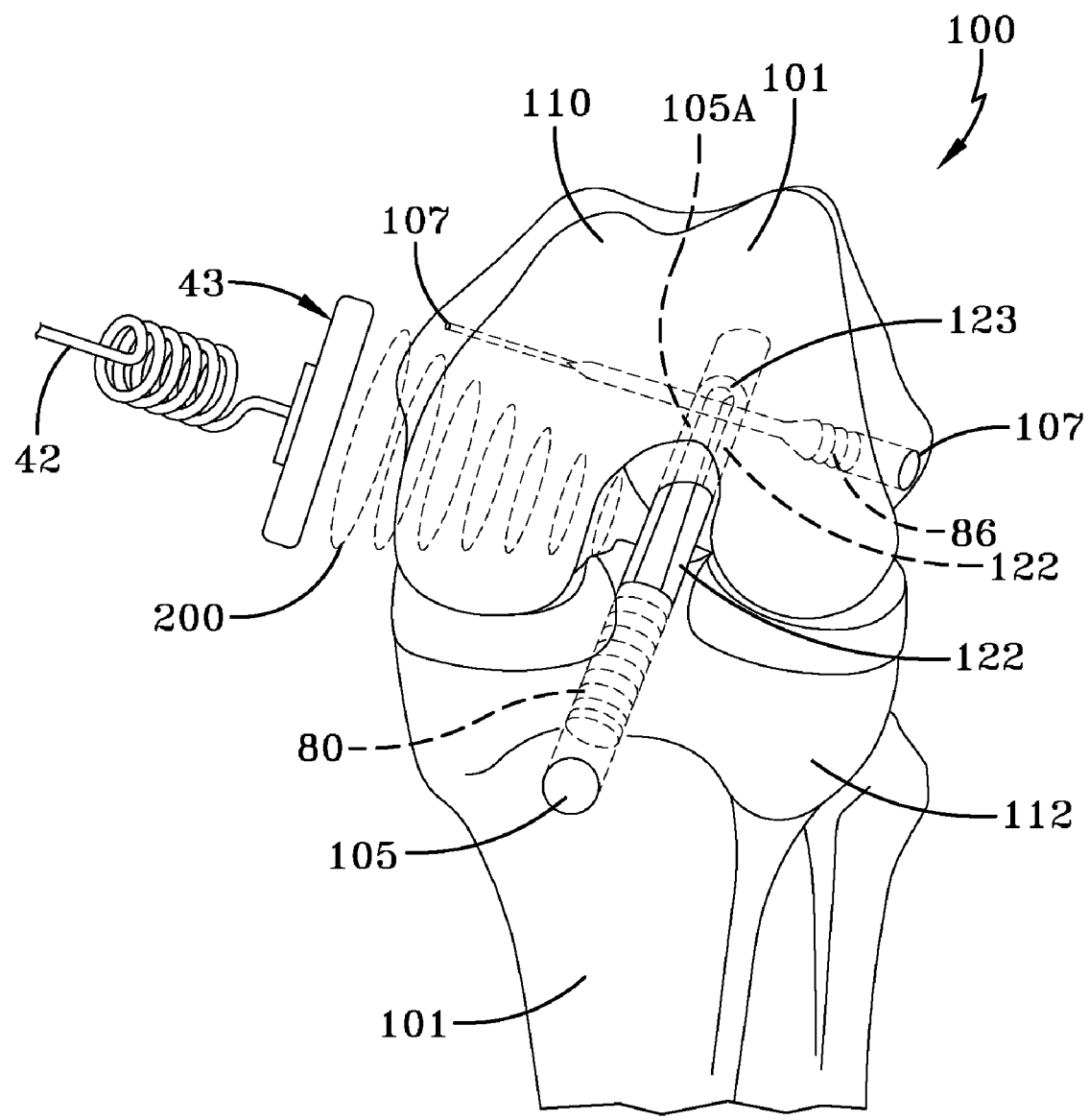
FIG. 16 is a perspective view of the tendon having been attached and a shock wave treatment being applied at the surgical site.

With reference to FIGS. 15 and 16 a method of loading tendons 122 into the knee is illustrated wherein the surgical method for loading ligament grafts into a joint is taught whereby a longitudinal socket 105 formed in a bone is intersected by a transverse pin. A flexible strand 90 is drawn with the pin through the bone; a loop portion of the strand is diverted so it protrudes out of the entrance to the longitudinal socket. The ends of the strands remaining accessible on either side of bone 101 through the opening 107. The ligament graft or tendon 122 is captured within the strand loop 92 protruding from the entrance of the socket 105. The strand 90 is retracted into the socket drawing the graft 122 into the socket by pulling on accessible ends of the flexible strand with forceps 88. The graft 122 is fixed in the socket 105 using the transverse implant or pin 86 which is located in the opening 107.

As shown in FIG. 16, the transverse implant or pin 86 passes through a loop 123 created in the tendon or ligament 122 in such a fashion that the tendon or ligament 122 is securely maintained in the upper joint 110 relative to the lower joint 112 after which a screw 80 of the interference type is passed through the tibial tunnel 105 in order to fix the graft 122 wherein the femoral tunnel 105A is narrow so the tendon fits snugly within the tibial tunnel 105 in the femoral socket thus avoiding wiping of the tendons 122 along the implant. This procedure is as taught in U.S. Pat. No. 6,537,319 the subject matter of which is incorporated herein by reference in its entirety.

With further reference to FIG. 16, it is noted that a shock wave applicator or head 43 is placed on the surgical site near to or in proximity to the ligament 120 or tendon 122 being attached. The shock wave will transmit preferable low energy shock waves 200 to the treated area such that the shock waves will induce and stimulate rapid healing of the surgical site. Additionally the area surrounding and including the surgical wound get a stimulation induced by the shock waves wherein the muscle and skin tissue more rapidly heal which greatly enhances recovery. This is close in part to living tissue exposed to shock waves, particularly those cut or otherwise damaged during surgery having an impaired regeneration of cells and growth of new tissue after being exposed to shock waves particularly low energy or unfocused waves that induce growth without causing any undue and harmful cellular hemorrhaging. These and other benefits of shock wave treatments in combination with the anchoring of soft tissue such as ligaments, tendons, muscle or cartilage to bone mass to be described hereinafter.

In each of the representative treatments as shown in FIGS. 14 through 16 the shockwave applicator can be used within a sterile sleeve or covering and may simply be disinfected using a suitable antimicrobial disinfecting agent prior to use. Alternatively the applicator may be sterilized when used without a sterile sleeve. The sleeves or coverings are preferably disposable and should be discarded after use. When treating any tissue or organ the sterile sleeve holding the applicator or in the case of using the applicator without a sleeve the tissue contacting surface should be coupled acoustically by using known means such as sterile fluids or viscous gels like ultrasound gels or even NaCl solutions to couple the transmitted shock wave into the organ in an aseptic sterile fashion.

In each of the above described surgical procedures a complimentary shock wave method of treating the surgical site 100 with an at least partially exposed target site on the surgical area or volume wherein the area to be treated, hereinafter referred to as the target site 100, is positioned in a convenient orientation to permit the source of the emitted waves 200 to most directly send the waves unobstructed to the target site to initiate shock wave stimulation of the soft tissue, tendon 122, ligament 120 or cartilage within target area 100 with minimal preferably no interfering tissue or bone 101 features in the path of the emitting source or lens. Assuming the target area 100 is within a projected area of the wave transmission, a single transmission dosage of wave energy may be used. The transmission dosage can be from a few seconds to 20 minutes or more depending on the condition. Preferably the waves are generated from an unfocused or focused source. The unfocused waves can be divergent or near planar and having a low pressure amplitude and density in the range of 0.00001 $mJ/mm^2$ to 1.0 $mJ/mm^2$ or less, most typically below 0.2 $mJ/mm^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the treated tissues do not have to experience the sensation of hemorrhaging so common in the higher energy focused wave forms having a focal point at or within the targeted treatment site.

If the target site 100 is subjected to a surgical procedure as described above, exposing at least some if not all of the tissue or bone mass within the target surgical site 100 may require that the patient or the generating source must be reoriented relative to the site and a second, third or more treatment dosage can be administered. The fact that the dosage is at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient, particularly when bone mass was being impinged by the transmitted shock waves. The use of low energy focused or un-focused waves at the target site enables multiple sequential treatments in an almost pain free way.

The present method does not rely on precise site location per se due in part to the fact that the shock waves are not focused to impinge at a precise point. The physician's general understanding of the anatomy of the patient should be sufficient to locate the target area to be treated. This is particularly true when the exposed tissue is visually within the surgeon's line of sight and this permits the lens or cover of the emitting shock wave source to impinge on the tissue directly during the shockwave treatment. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating stem cell activation or a cellular release or activation of VEGF and other growth factors.

This methodology is also useful in stimulating enforcement of defense mechanisms in tissue cells to fight infections from bacteria and can be beneficially used germicidally to treat or cleanse the surgical wounds and surrounding tissue which is a primary concern in these procedures.

The implications of using the (re)generative features of this type of shock wave therapy are any weakened soft tissue or bone can be strengthened to the point of reducing or eliminating the risk of irreparable damage or failure. This regenerative feature is quite valuable in reconstruction, repair, or transplanting of tendons, ligaments, cartilage or muscle tissue onto a bone mass.

The use of the shock wave in combination with the above described surgical procedure as part of the surgical operation provides the fastest stimulation of the treatment site. In addition the patient may benefit by the use of stimulating shock wave treatments post operatively by receiving one or more separate treatments over a period of time to periodically stimulate the cells within the tissue. These shock wave treatments improve vascularization and tissue growth it is believed by stimulating otherwise dormant stem cells within the body and by causing a release of healing agents and growth factors all of which contribute to more rapid healing and attachment to the underlying bone mass.

To better appreciate how shock waves work one must gain an appreciation of the apparatus and devices used to generate such wave patterns.

Applicants have applied this treatment therapy to cartilage and tendon orthoscopic repairs and have reduced the healing time from over 6 weeks to less than 2 weeks. These and other beneficial treatments are made possible by using an apparatus with a shock wave emission either singularly or in an array as described below in the embodiments shown in FIGS. 1-12. As shown in FIG. 16 the shock waves are illustrated as 200, it is understood that each of the shock wave patterns illustrated in FIGS. 1-12 are intended to be available for use in the inventive treatment therapy as described herein.

Figure 1A:
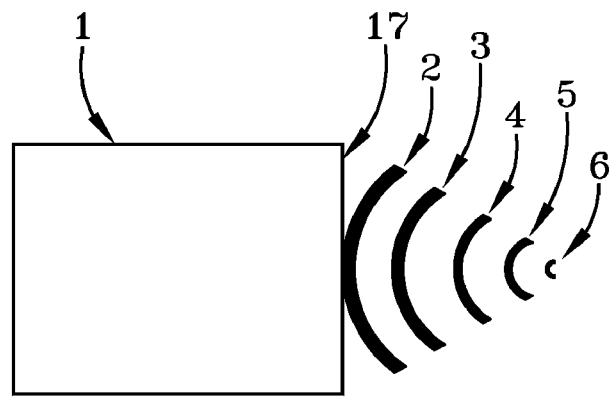
FIG. 1a is a simplified depiction of a pressure pulse/shock wave (PP/SW) generator with focusing wave characteristics.

FIG. 1*a* is a simplified depiction of the a pressure pulse/ shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat tissue. The tissue is generally located in or near the focal point which is located in or near position 6. At position 17 a water cushion or any other kind of exit window for the acoustical energy is located.

Figure 1B:
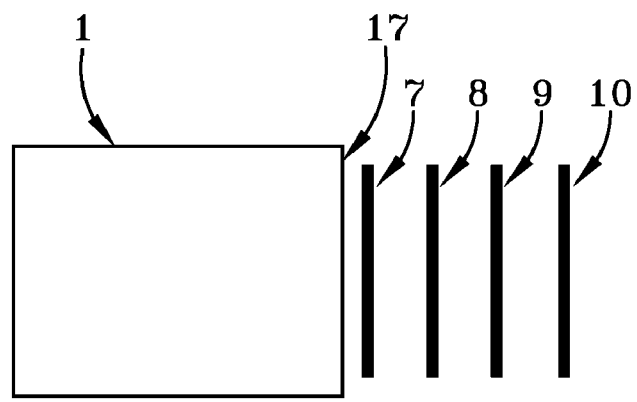
FIG. 1b is a simplified depiction of a pressure pulse/shock wave generator with plane wave characteristics.

FIG. 1*b* is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
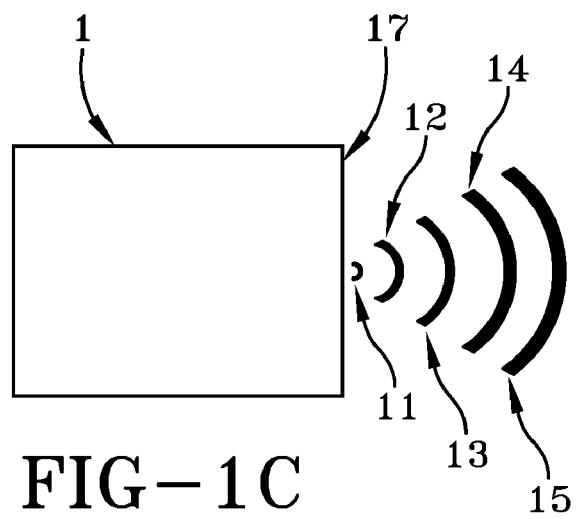
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion. The divergent characteristics of the wave front may be a consequence of the mechanical setup shown in FIG. 2b.

Figure 2A:
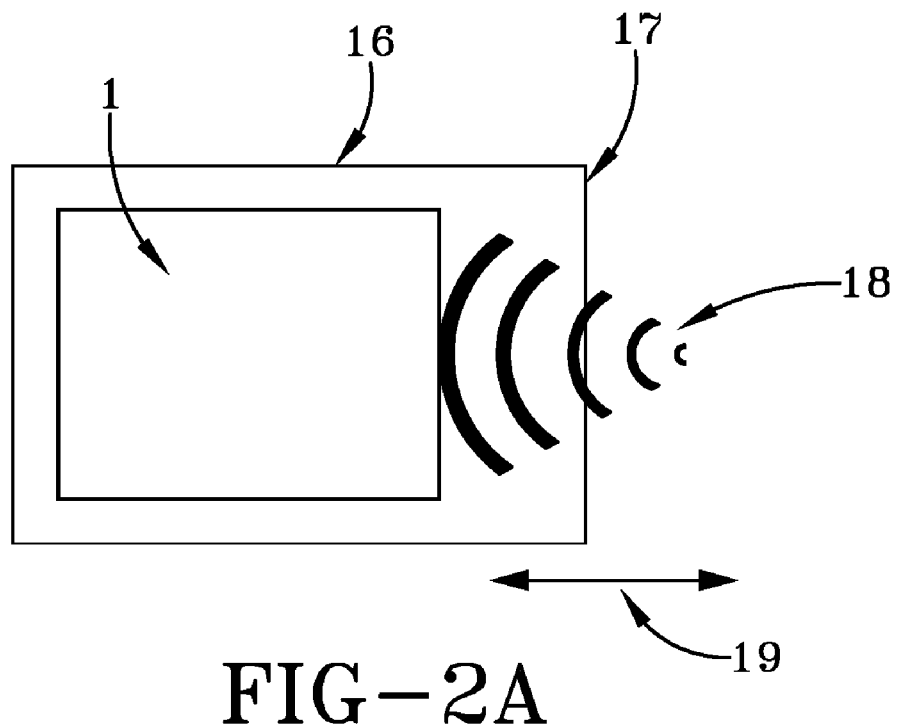
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
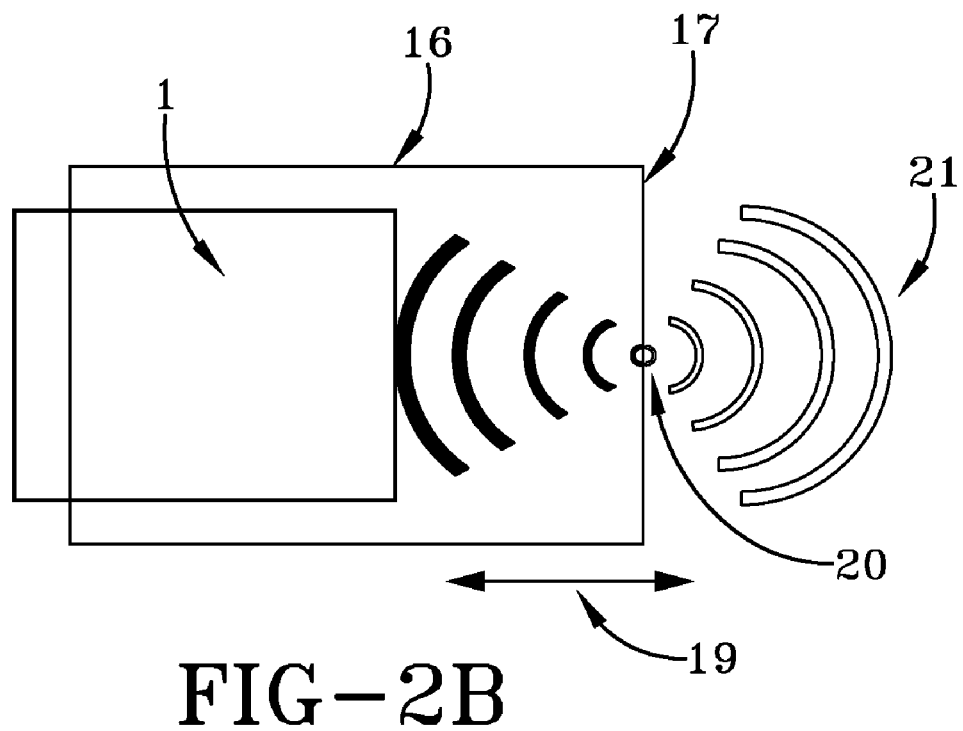
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
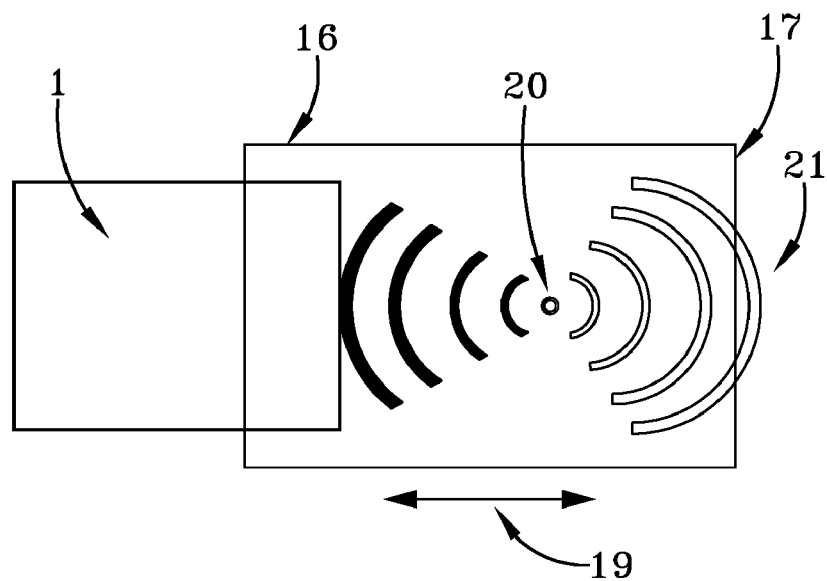
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, nearly plane or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in drawings 1a-1c and 2a-2c are independent of the generation principle and thus are valid for not only electro-hydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
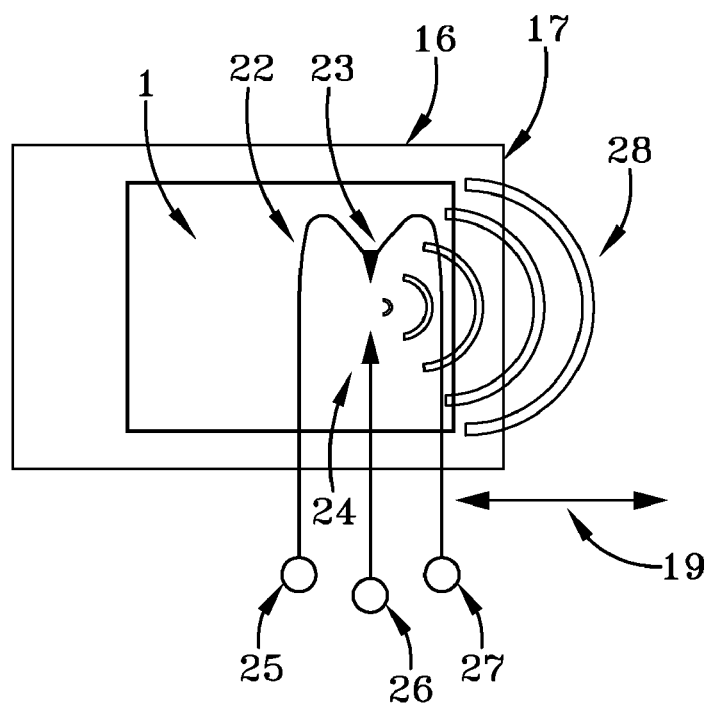
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
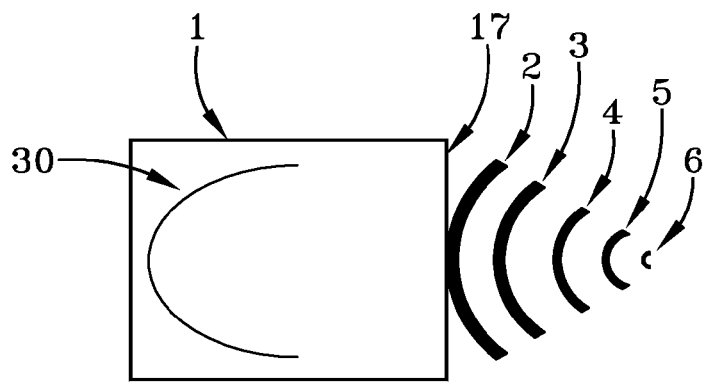
FIG. 4a is a simplified depiction of a pressure pulse/shock wave generator having a focusing element in the form of an ellipsoid. The waves generated are focused.

FIG. 4a is a simplified depiction of the pressure pulse/shock wave generator (shock wave head) having as focusing element an ellipsoid (30). Thus, the generated waves are focused at (6).

Figure 4B:
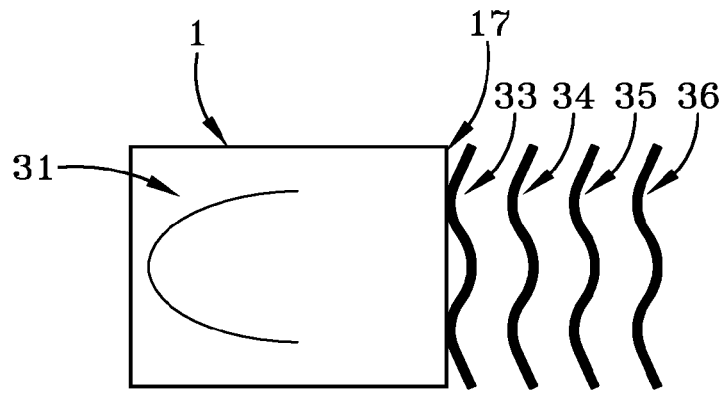
FIG. 4b is a simplified depiction of a pressure pulse/shock wave generator having a parabolic reflector element and generating waves that are disturbed plane.

FIG. 4b is a simplified depiction of the pressure pulse/shock wave generator (shock wave head) having as a focusing element a paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
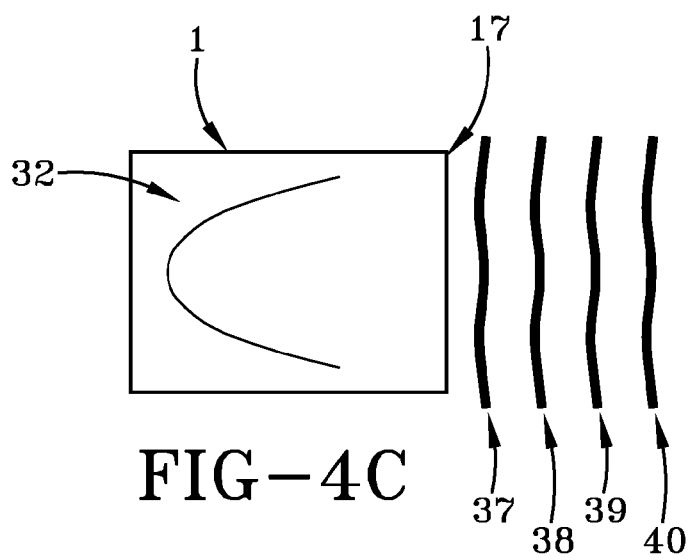
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/shock wave generator (shock wave head) having as a focusing element a generalized paraboloid ($y^n=2px$, with $1,2<n<2,8$ and $n\neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
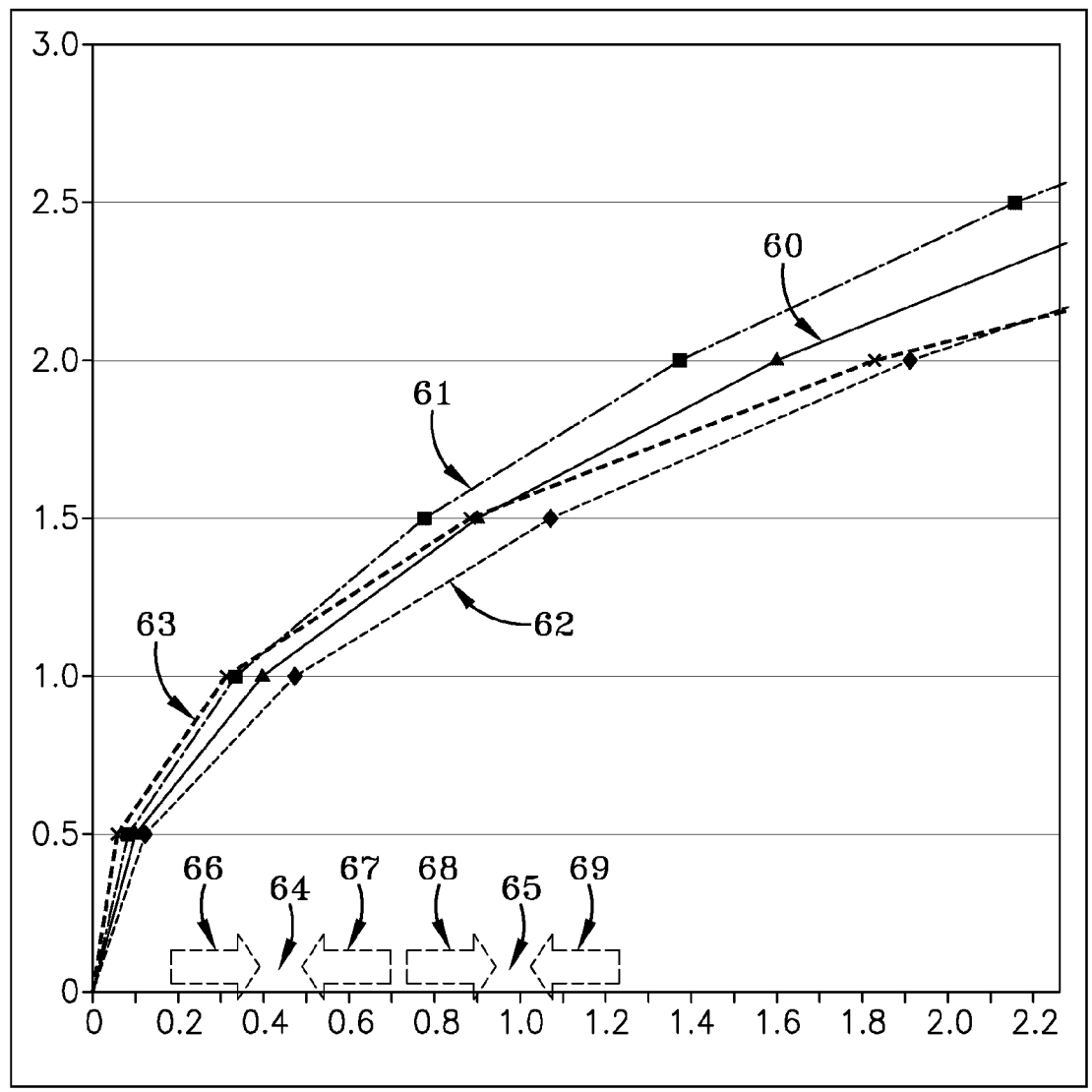
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n\neq 2$ and a p value of about 1.55 cm. The generalized paraboloid compensates for different p values that result from the electrode burn down and/or adjustment of the electrode tips.

Figure 5:
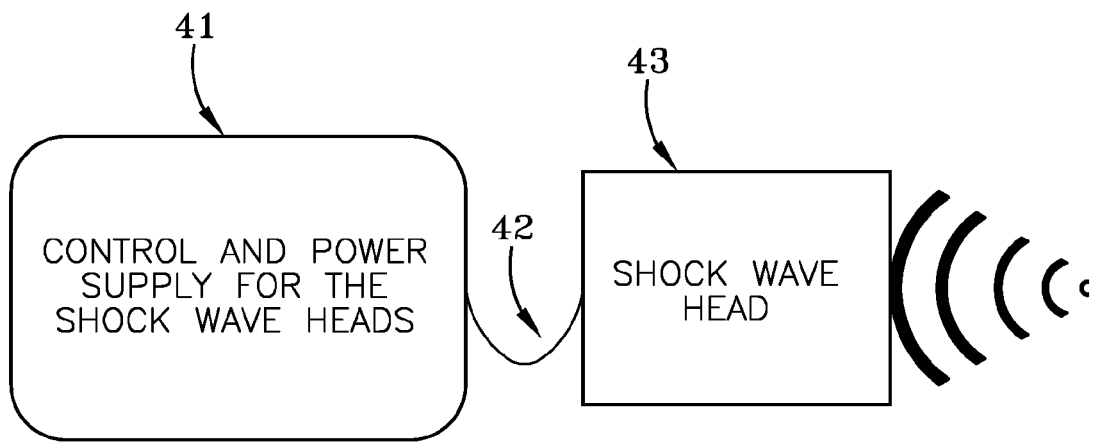
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
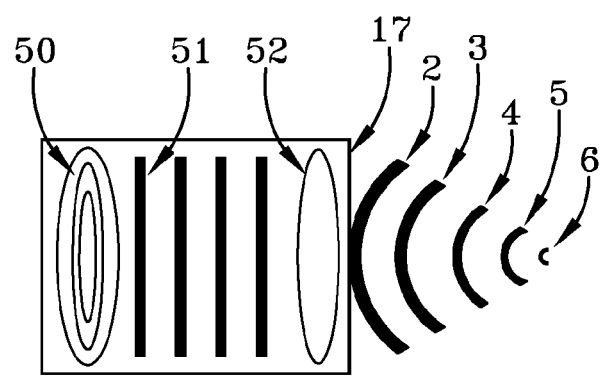
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
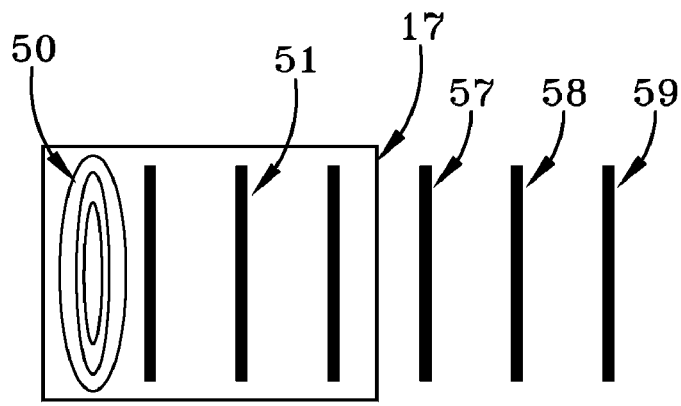
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
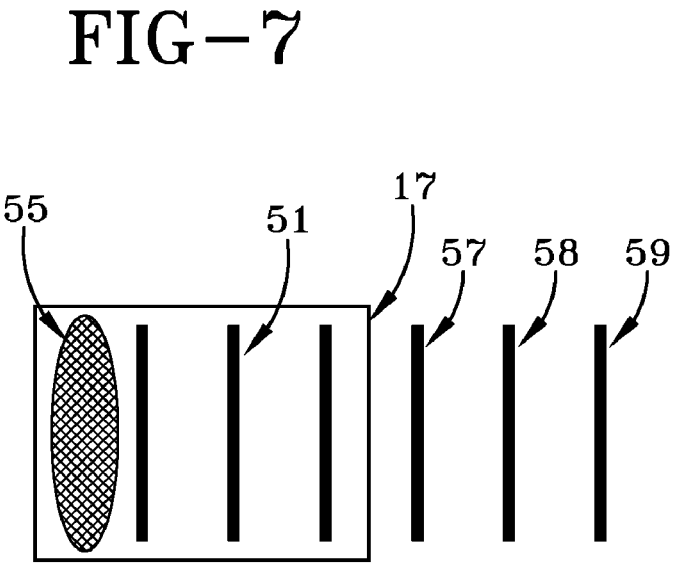
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
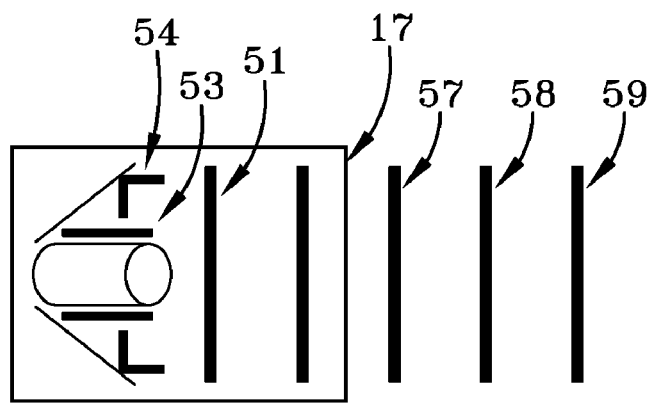
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
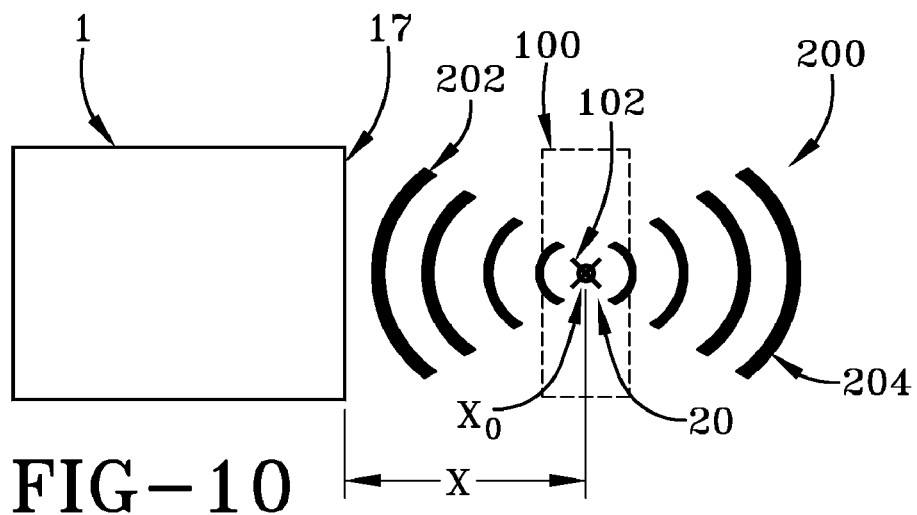
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
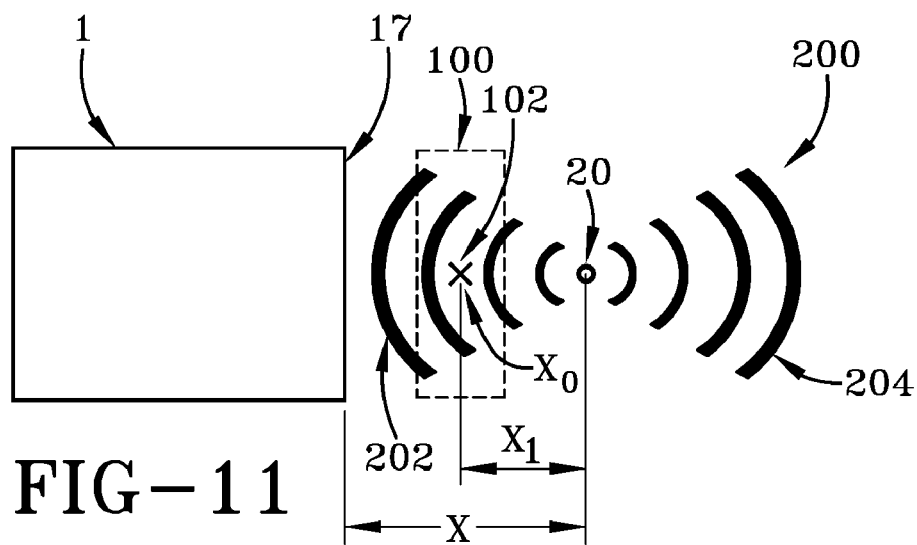
FIG. 11 is a simplified depiction of a pressure pulse/shock wave (PP/SW) generator with the focusing wave characteristics shown wherein the focus is located a distance $X_1$ from the location $X_0$ of an organ wherein the converging waves impinge the organ.
Figure 12:
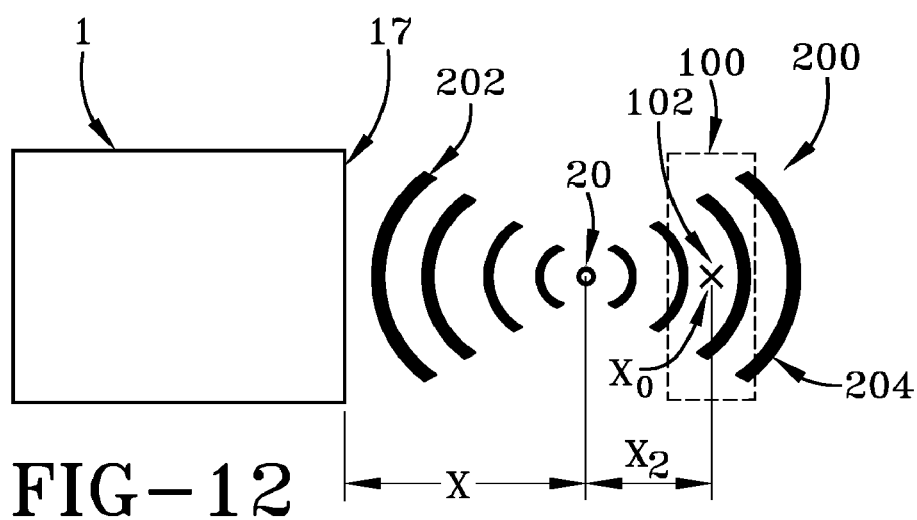
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a tissue or target site 100 is shown generally centered on the focal point or volume 20 at a location $X_0$ within the target site 100. In this orientation the emitted waves are focused and thus are emitting a high intensity acoustic energy at the location $X_0$. This location $X_0$ can be anywhere within or on the target site. Assuming the tissue 100 has a mass 102 at location $X_0$ then the focus is located directly on the mass 102. In one method of treating a tumor or any other type mass 102 these focused waves can be directed to destroy or otherwise reduce the mass 102.

With reference to FIG. 11, the target site 100 is shifted a distance X toward the generator or source 1. The target site 100 at location $X_0$ being positioned a distance $X-X_1$ from the source 1. This insures the site 100 is impinged by converging waves 202 but removed from the focal point 20. When the site 100 is tissue this bombardment of converging waves 202 stimulates the cells activating the desired healing response as previously discussed.

With reference to FIG. 12, the target 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the tissue 100 which when the cellular tissue is a ligament, tendon or cartilage attached on or in a bone mass stimulates the cells to produce the desired healing effect or response.

It is believed that the use of low energy shock waves to promote rapid healing and provide a germicidal infection barrier is a first use. The method stimulates tissue attachment to bone mass and is particularly valuable when such tissues have to be mechanically held in place by implanted anchors and fasteners. Furthermore these treatments accelerate bone growth thereby helping any openings or drilled holes to more rapidly close. The benefits to the patent are reduced risk of infection and more rapid healing in a relatively pain free use of these low energy shock waves.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. The method of attaching or reattaching a ligament, tendon or other soft tissues to a bone mass comprises the steps of:
   positioning or placing the ligament, tendon, cartilage or other soft tissue in or adjacent to the bone mass;
   anchoring or otherwise fastening the ligament, tendon, cartilage or other soft tissue to the bone mass;
   transmitting pressure pulses including very fast pressure pulses called acoustic shock waves to the ligament, tendon, cartilage or other soft tissue and the bone mass from a pressure pulse shock wave generator or source wherein the pressure pulses or acoustic shock waves are acoustic pulses which includes several cycles of positive and negative pressure, wherein the pressure pulse has an amplitude of the positive part of such a cycle above 0.1 MPa and the time duration of pressure pulse cycle is from 1 microsecond (µs) to a second (s), rise times to the peak pressure of the positive part of the first pressure cycle is in the range of 1 nano-second (ns) to 1 milli-second (ms), the acoustic shock waves being very fast pressure pulses having amplitudes of the positive part of the cycle similarly above 0.1 MPa but with rise times to a peak pressure of the positive part of the amplitude being below 100 ns, the duration of the shock wave is below 3 µs for the positive part of a cycle and above 1 µs for the negative part of a cycle; and
   subjecting the ligament, tendon, cartilage or other soft tissue and the bone mass to convergent, divergent, planar or near planar acoustic shock waves or pressure pulses in the absence of a focal point impinging the soft tissue and bone mass stimulating a cellular response in the absence of creating cavitation bubbles evidenced by not experiencing the sensation of cellular hemorrhaging caused by the emitted waves or pulses in the soft tissue wherein the cellular soft tissue is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the cellular soft tissue or beyond the cellular soft tissue thereby passing the emitted waves through the cellular soft tissue while avoiding having any localized focal point within the cellular soft tissue wherein the pressure pulse shock wave generator or source is based on electro-hydraulic, electromagnetic, piezoceramic or ballistic wave generation having an energy density value ranging from 0.00001 mJ/mm² to 1.0 mJ/mm².

2. The method of claim 1 wherein the pressure pulses or acoustic shock waves are transmitted during the surgical procedure after anchoring or otherwise fastening the ligament, tendon, cartilage or other soft tissue.

3. The method of claim 1 wherein the pressure pulses or acoustic_shock waves are transmitted post operatively in one or more treatment dosages.

4. The method of claim 1 wherein the transmitted pressure pulses or acoustic shock waves are divergent or near planar or wherein the emitted shock waves are convergent having a geometric focal volume or point at a distance of at least X from a generator or source, the method further comprising positioning the ligament, tendon, cartilage or other soft tissue at a distance less than the distance X from the source.

* * * * *